United States Patent [19]

Fox, Jr. et al.

[11] Patent Number: 4,522,819
[45] Date of Patent: Jun. 11, 1985

[54] 1-ETHYL-6-FLUORO-1,4-DIHYDRO-4-OXO-7-(1-PIPERAZINYL)-3-QUINOLINE CARBOXYLIC ACID AND METAL SALTS THEREOF USEFUL IN BURN THERAPY

[75] Inventors: Charles L. Fox, Jr., Sherman, Conn.; Shanta M. Modak, River Edge, N.J.

[73] Assignee: Norwich Eaton Pharmaceuticals, Inc., Norwich, N.Y.

[21] Appl. No.: 391,452

[22] Filed: Jun. 23, 1982

Related U.S. Application Data

[63] Continuation of Ser. No. 193,307, Oct. 2, 1980, abandoned.

[51] Int. Cl.$^3$ ............... C07D 401/10; A61K 31/495; A61K 31/555; A61K 31/47
[52] U.S. Cl. .................... 514/187; 544/225; 544/363; 514/255
[58] Field of Search ..................... 424/245; 544/225

[56] References Cited

U.S. PATENT DOCUMENTS

| | | | |
|---|---|---|---|
| 4,017,622 | 4/1977 | Minami | 424/250 |
| 4,146,719 | 3/1979 | Irikura | 544/363 |
| 4,292,317 | 9/1981 | Pesson | 424/250 |

OTHER PUBLICATIONS

Hiroshi et al., Chem. Abs. 93, 198382 (1980).

Primary Examiner—Mark L. Berch
Attorney, Agent, or Firm—Cooper, Dunham, Clark, Griffin & Moran

[57] ABSTRACT

1-Ethyl-6-fluoro-1,4-dihydro-4-oxo-7-(1-piperazinyl)-3-quinoline carboxylic acid and metal salts thereof wherein the metal moiety is selected from the group consisting of silver, zinc, cerium and cobalt are useful in the treatment of burns. These compounds may be applied to the affected surface of a burn victim either directly or as part of a composition together with a physiologically acceptable carrier, such as a water-dispersible, hydrophilic carrier.

23 Claims, No Drawings

1-ETHYL-6-FLUORO-1,4-DIHYDRO-4-OXO-7-(1-PIPERAZINYL)-3-QUINOLINE CARBOXYLIC ACID AND METAL SALTS THEREOF USEFUL IN BURN THERAPY

This is a continuation of application Ser. No. 193,307 filed Oct. 2, 1980.

BACKGROUND OF THE INVENTION

Despite the development of effective topical and systemic antibiotics, invasive wound sepsis and septicemia from pseudomonas aeruginosa remain a problem in seriously burned patients. Emergence and development of drug resistant species of bacteria have defied the control obtained through the regimen of potent antibiotics. In recent years numerous reports of gentamicin resistant gram negative organisms (Shulman, J. A., Terry, P. M. Hough, C. E.: Colonization with a gentamicin resistant pseudomonas aeruginosa pyocine type 5 in a burn unit. *J. of Inf. Diseases* 124:S18, 1971), especially pseudomonas, have appeared in the literature. (Snelling, C. F. T., Ronald, A. R., Cates, C. Y., et al.; Resistance of gram negative bacilli to gentamicin *J. of Inf. Diseases* 124:S264, 1971; Chadwick, P: Resistance of pseudomonas aeruginosa to gentamicin. *Canadian Med. Assoc.* J. 109:585, 1973; Bryan, L. E., Shadrabadi, M. S., Van Denelzen, H. M.: Gentamicin resistance in pseudomonas aeruginosa. R-factor mediated resistance. *Antimicrobial Agents and Chemotherapy* 6:191, 1974). Although silver sulfadiazine (AgSD), the most promising topical agent in the treatment of burn wound infections in this decade (Fox, Jr., C. L.: A new topical therapy for pseudomonas in burns. *Arch. Surg.* 96:184, 1968; Fox, Jr., C. L. Rappole, B. W., Stanford, J. W.: Control of pseudomonas infection in burns by silver sulfadiazine. *Surg. Gyn. Obstr.* 128:1021, 1969), appeared to surmount these problems, pseudomonas infections resistant to silver sulfadiazine treatment have been reported recently in burned patients (Gayle, W. E., Mayhall, C. G., Lamb, A., et al: Resistant enterobacter cloacal in a burn center. The ineffectiveness of silver sulfadiazine. *J. of Trauma* 18:327, 1978; Heggers, J. P., Robson, M. C.: The emergence of silver sulfadiazine resistant *pseudomonas aeruginosa. Burns* 5:184, 1978).

Similar occurrence of occasional AgSD resistant pseudomonas infections in patients have been observed in other parts of the world. Several such resistant strains have been obtained and the nature of their resistance studied in an experimental burn model. This investigation revealed an unusual phenomena, namely, normal sensitivity of pseudomonas to AgSD in vitro, but resistance to topical AgSD therapy in infected burn wounds in mice and rats. (Modak, S., Stanford, J. W., Bradshaw W., Fox, Jr., C. L.: Silver sulfadiazine resistant pseudomonas infection in experimental burn wounds. 3rd Intrl. Congr. of Pharma. Treatment of Burns, 1980 (in press) ed. Donati L., Burke, J., Bertelli, A., Italy.)

Comparative studies of the virulence and drug sensitivity of in vivo AgSD sensitive and nonsenstive strains were carried out to investigate the possible mechanism of in vivo resistance. Since all the resistant strains obtained from burn patients appeared to be senstive in vitro, the evaluation of a topical agent for its effectiveness was determined in experimental burn models. Several other antibacterial agents known to be effective in vitro were also ineffective against these strains.

The continued search for an effective topical agent has led to the discovery that a synthetic analogue of nalidixic acid, 1-ethyl-6-fluoro-1,4-dihydro-4-oxo-7-(1-piperazinyl)quinolinecarboxylic acid possesses high antipseudomonas activity in vitro (Ito, A., Hira, K., Inoue, M., et al: In vitro antibacterial activity of AM-715, a new nalidixic acid analog. *Antimicrobial Agents and Chemotherapy* 17:103, 1980, and French Pat. Nos. 879,106 and 870,576) are effective in controlling AgSD resistant pseudomonas infections in burned mice.

SUMMARY OF THE INVENTION

Specifically, it has been found that 1-ethyl-6-fluoro-1,4-dihydro-4-oxo-7-(1-piperazinyl)-3-quinoline carboxylic acid and metal salts thereof wherein the metal moiety is selected from the group consisting of silver, zinc, cerium and cobalt are useful in the treatment of surface infections and of burns in animal and man. These compounds may advantageously be applied to the affected surface of a burn victim either directly or as part of a composition with a physiologically acceptable carrier, such as a water-dispersible hydrophilic carrier, in effective antibacterial amounts.

DETAILED DESCRIPTION OF THE INVENTION 1-ethyl-6-fluoro-1,4-dihydro-4-oxo-7-(1-piperazinyl)-3-quinoline carboxylic acid has the structure:

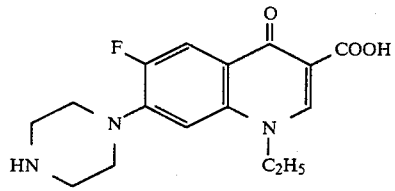

This compound is known to have high antibacterial activity in vitro against standard bacterial strains such as *B. subtilis, S. aureus, P. aeruginosa*, and *E. coli* strains. Ito, A. et al., *Antimicrobial Agents and Chemotherapy* 17:103,1980, supra.

However, unlike several other compounds which have high in vitro antibacterial activity, but are ineffective in controlling silver sulfadiazine resistant pseudomonas infections in burned mice, this compound and metal salts thereof such as silver, zinc, cerium, and cobalt salts, unexpectedly are effective in controlling such infections.

These compounds may be applied directly to the surface of burn wounds or may be employed as a component of a composition along with a physiologically acceptable carrier. Whether employed directly or in a composition, the compounds should be applied in effective antibacterial amounts. Such amounts may vary widely depending upon the bacterial strain involved, but typically will vary from about 0.001 percent to about 10.0 percent by weight, preferably from about 0.01 percent to about 1.0 percent when the compounds are employed in compositions.

As indicated hereinabove, 1-ethyl-6-fluoro-1,4-dihydro-4-oxo-7-(1-piperazinyl)-3-quinoline carboxylic acid is a known compound which may be obtained directly or synthesized by known methods. Metal salts thereof wherein the metal moiety is silver, zinc, cerium, or cobalt, are novel compounds which are also useful in burn therapy and may unexpectedly provide superior results when compared with the carboxylic acid itself. These metal salts may be prepared as follows.

The sodium salt of 1-ethyl-6-fluoro-1,4-dihydro-4-oxo-7-(1-piperazinyl)-3-quinoline carboxylic acid may be prepared by adding an equimolar amount of sodium hydroxide. Each metal salt may then be prepared by reacting the sodium salt with a stoichiometric quantity of a metal salt such as silver nitrate, cerous chloride, zinc nitrate, or the like. Of the metal salts, the silver salt has been found to be particularly effective.

When the compound or a metal salt thereof are employed in a composition with a physiologically acceptable carrier, the carrier is desirably a conventional water-dispersible, hydrophilic carrier, particularly a conventional semi-soft or cream-like, water-dispersible or water-soluble, oil-in-water emulsion, which may be applied to an affected burn surface with a minimum of patient discomfort.

Suitable compositions may be prepared by merely incorporating or homogeneously admixing finely divided compound with the hydrophilic carrier or base or ointment. One technique in accordance with this invention for incorporating the silver compound in a hydrophilic ointment, such as an oil-in-water emulsion, involves reacting equimolar aqueous solutions of silver nitrate and the sodium salt of the compound to yield a white precipitate which is the silver salt. The resulting precipitate, after washing and drying, is then mixed or blended with the candidate hydrophilic ointment, such as the oil-in-water emulsion, to yield a composition comprising the silver salt dispersed in the ointment.

Compositions in accordance with this invention containing the compound or a metal salt dispersed in a water-dispersible hydrophilic carrier or ointment, e.g., a hydrophilic oil-in-water emulsion, are usually characterized by the following components and percentages by weight set forth in accompanying Table I:

TABLE I

| Component | % By Weight |
|---|---|
| Petrolatum | 0–25 |
| Water-insoluble $C_{16}$–$C_{22}$ fatty alcohol | 7–45 |
| Emollient | 0–15 |
| Emulsifying Agents, preferably non-ioinic | 4–16 |
| Humectant | 7–40 |
| Compound or salt | 0.001–10 |
| Preservative | 0–0.3 |
| Deionized or Distilled Water q.s. | 100 |

The fatty alcohols, stearyl alcohol, cetyl alcohol, lauryl alcohol and myristyl alcohol are useful in the preparation of compositions in accordance with this invention. These preferential oil-soluble fatty alcohols act as a stiffener in the resulting composition. As the emollient, isopropyl myristate, lanolin, lanolin derivatives, isopropyl palmitate, isopropyl stearate and the corresponding sebacates and other known emollients are suitable. As the emulsifying agent sorbitan monooleate, such as an amount in the range 0.5–4 percent by weight, and polyoxyl 40 stearate in an amount in the range 7–12 percent by weight, both non-ionic emulsifying agents are satisfactory. A suitable humectant would be propylene glycol, sorbitol or glycerin or mixtures thereof, all being water-soluble compounds. A suitable preservative would be any of the useful conventional water-soluble preservatives which exhibit antimicrobial activity, such as sorbic acid, benzoic methylparaben, propylparaben, and mixtures thereof.

In the formulation of a composition having the makeup set forth in Table I hereinabove, as the amount of aqueous phase is increased, the solid content, i.e., the water-immiscible or water-insoluble components, e.g., fatty alcohol, such as stearyl alcohol, and/or petrolatum, must also be increased relatively to help stiffen the composition. The preservative, e.g., methylparaben, is employed in the formulation only as a preservative for the overall composition and, as indicated, methylparaben was found to be a satisfactory preservative. Methylparaben, as indicated, however, may also be used in combination with propylparaben.

Accordingly, compositions useful in the practices of this invention would include compositions comprising 0–25 percent by weight petrolatum, 7–45 percent by weight stearyl alcohol, 0–15 percent by weight isopropyl myristate, 5–20 percent by weight of an emulsifying agent, 7–40 percent by weight propylene glycol, 0.001–10 percent by weight compound or metal salt, the remainder being water, as required to bring the total percentages to 100 percent. Other compositions useful would include compositions consisting essentially of 0.01–1.0 percent by weight compound or salt, 7–8 percent by weight propylene glycol, 38–44 percent by weight water, 14–18 percent by weight petrolatum, 14–18 percent by weight stearyl alcohol, 5–8 percent by weight isopropyl myristate, 0.5–2 percent by weight sorbitan monooleate and 6–10 percent by weight polyoxyl 40 stearate. Another composition useful in the practice of this invention would include the composition consisting essentially of 0–25 percent by weight petrolatum, 7–45 percent by weight of an aliphatic fatty alcohol having a carbon atom content in the range $C_{16}$–$C_{22}$, 0–15 percent by weight of an emollient, 7–16 percent by weight of an emulsifying agent, 7–14 percent by weight of a humectant and 0.01–1.0 percent by weight of the compound or one of its metal salts.

The results of various experiments illustrating the practices of this invention are now set forth.

EXPERIMENTAL DETAILS

Methods and Materials

Bacterial Strains: *Ps. Boston* was the strain used in our previous investigations (Fox, Jr., C. L., Sampath, A. C., Stanford, J. W.: Virulence of pseudomonas infection in burned rats and mice. *Arc. Surg.* 101: 508,1970); Ps. Mangalore was isolated from a burn patient in Kasturba Medical College, Mangalore, India; Ps. 181 was obtained from Hopital de los Ninos, Lima, Peru; and AgSD resistant *Ps. Boston* was produced in our laboratory by repeatedly growing this organism in medium containing increasing amounts of AgSD.

In vitro assay of microbial inhibition: Inhibition indices are obtained by tube dilution tests using nutrient broth. Growth in the presence and absence of drugs was observed by turbidity measurement after incubation at 37° C. for 24–48 hours (Fox, Jr., C. L., Modak, S. M., Stanford, J. W.: Cerium sulfadiazine as a topical agent for burn wound infections: A comparison with silver sulfadiazine and zinc sulfadiazine. *Burns* 4:233,1978).

Animal experiments: Mice (female Swiss 18–22 grams) received scalds using methods reported previously (Fox, Jr., C. L.: A new topical therapy for pseudomonas in burns. *Arch. Surg.* 96:184,1968; Fox, Jr., C. L., Sampath, A. C., Stanford, J. W.: Virulence of pseudomonas infection in burned rats and mice. *Arch. Surg.* 101:508, 1970; Fox, Jr., C. L., Modak, S. M., Stanford, J. W.: Cerium sulfadiazine as a topical agent for burn wound infections: A comparison with silver sulfadiazine and zinc sulfadiazine. *Burns* 4:233, 1978). The wounds were contaminated one hour post burn with freshly prepared 18–20 hour broth culture of pseudomonas diluted to optical density 0.30. Infection was induced by immersing the tail in the culture.

The first treatment was administered 4 hours post infection by rubbing the medicated creams over all burned surfaces. All drugs used were mixed in a cream base such as described hereinabove. Thereafter, all animals were observed and treated once daily. The primary criterion was survival. Animals that succumbed were autopsied and the cardiac blood cultured to verify the presence of pseudomonas.

RESULTS

In vitro tests: The minimum inhibitory concentrations (MIC) of 1-ethyl-6-fluoro-1,4-dihydro-4-oxo-7-(1-piperazinyl)-3-quinoline carboxylic acid against various bacteria are shown in Table 2. Ps. Boston, Ps. Mangalore and Ps. 181 were sensitive to 0.05 to 0.1 $\mu$mole/ml AgSD whereas the MIC of the carboxylic acid against these organisms were as low as 0.004–0.008 $\mu$mole/ml.

In the case of E. coli, staph, aureus, klebsiella and proteus, the MIC of the carboxylic acid is about 1/20 less than that of silver sulfadiazine.

TABLE 2

Antimicrobial Sprectrum of Silver Sulfadiazine and 1-Ethyl-6-fluoro-1,4-dihydro-4-oxo-7-(1-piperazinyl)-3-quinoline carboxylic acid

| Organism | MIC ($\mu$mole/ml) | |
|---|---|---|
| | AgSD | Carboxylic Acid |
| Pseudomonas Boston | 0.05 | 0.004 |
| Pseudomonas Mangalore | 0.05 | 0.008 |
| Pseudomonas 181 | 0.1 | 0.008 |
| Escherichia Coli | 0.0125 | 0.006 |
| Staphylococcus Aureus | 0.05 | 0.003 |
| Kleb. Pneumoniae | 0.05 | 0.001 |
| Proteus vulgaris | 0.003 | 0.0002 |

5 ml of nutrient broth containing the drug was inoculated with 0.2 ml of $10^{-4}$ dilution of overnight culture.

0.1 $\mu$mole AgSD corresponds to 35.7 $\mu$g 0.1 $\mu$mole carboxylic acid corresponds to 31 $\mu$g.

Inasmuch as wound exudates contain large amounts of proteins and chlorides, it is possible that some of the topical agent may react with these molecules and only the remainder will be available for the bacteria. To evaluate the extent of the loss of the antibacterial agent due to the exudate, the MIC of AgSD and the carboxylic acid against *Ps. Boston* and Ps. Mangalore grown in nutrient broth containing 10% human plasma was determined. The MIC of AgSD in the medium was 0.4 $\mu$mole/ml which is 8 times more than that in nutrient broth whereas it was the same for the carboxylic acid in both the media (Table 3).

In vivo effectiveness of various topical agents. To investigate whether the in vivo drug resistance observed in some of the pseudomonas strains is specific to AgSD, the efficacy of other commonly used as well as newly synthesized topical agents was tested in burned mice using AgSD resistant *Ps. Mangalore* and AgSD sensitive *Ps. Boston* as the infecting agents. The results are summarized in Table 4. All of the topical agents with the exception of Furacin, Sulfamylon acetate, and gentamicin sulfadiazine protected the mice completely against Ps. Boston infection but none of the topical agents were effective against Ps. Mangalore infection.

In vivo efficacy of 1-ethyl-6-fluoro-1,4-dihydro-4-oxo-7-(1-piperazinyl)-3-quinoline carboxylic acid In vivo efficacy of the carboxylic acid against *Ps. Mangalore*, Ps. 181 and AgSD resistant *Ps. Boston* was tested and compared with that of AgSD in burned mice and the results are summarized in Table 5. After infection with these resistant strains, the mortality with silver sulfadiazine therapy ranged from 80–100 percent by the 8th day post burn.

TABLE 3

Antimicrobial Activity of Silver Sulfadiazine and 1-ethyl-6-fluoro-1,4-dihydro-4-oxo-7-(1-piperazinyl)-3-quinoline carboxyoic acid Against Pseudomonas Grown in Nutrient Broth Containing 10 percent Plasma

| Organsim | Bacterial Dilution | MIC ($\mu$mole/ml) | |
|---|---|---|---|
| | | AgSD* | Carboxylic acid |
| Ps. Boston | $10^{-1}$ | 0.4 | 0.0125 |
| | $10^{-2}$ | 0.4 | 0.006 |
| Ps. Mangalore | $10^{-1}$ | 0.4 | 0.0125 |
| | $10^{-2}$ | 0.4 | 0.006 |

*In nutrient broth, MIC is 0.05 $\mu$/m. See TABLE 2.

0.2 ml of the overnight culture of the bacteria diluted to $10^{-1}$ and $10^{-2}$ was inoculated into 5 ml of nutrient broth containing 10 percent human plasma and the drug.

TABLE 4

Topical Therapy of Burned Mice Infected with *Ps. Mangalore* and *Ps. Boston*

| Topical Agents | Concentration | % Mortality (Days P.B.) | | | |
|---|---|---|---|---|---|
| | | Mangalore | | Boston | |
| | | 4 | 7 | 4 | 7 |
| None | — | 100 | 100 | 100 | 100 |
| Silver Sulfadiazine | 30 mM | 100 | 100 | 0 | 0 |
| Silver Sulfadiazine | 60 mM | 100 | 100 | 0 | 0 |
| Silver Sulfadiazine | 120 mM | 100 | 100 | 0 | 0 |
| Zinc Sulfadiazine | 30 mM | 100 | 100 | 0 | 0 |
| Cerium Sulfadiazine | 30 mM | 100 | 100 | 0 | 0 |
| Cobalt Sulfadiazine | 30 mM | 80 | 100 | 0 | 0 |
| Cobalt Sulfadiazine | 60 mM | 80 | 100 | — | — |
| Sodium Sulfadiazine | 90 mM | 100 | 100 | 0 | 20 |
| Tetracaine Sulfadiazine | 12 mM | 100 | 100 | 40 | 40 |
| Tetracaine Sulfadiazine | 30 mM | 100 | 100 | 0 | 0 |
| Tobramycin in SILVADENE[1] | 1% | 100 | 100 | — | — |
| EDTA in SILVADENE | 1% | 100 | 100 | — | — |
| Gentamicin in SILVADENE | 0.01% | 100 | 100 | — | — |
| Gentamicin in SILVADENE | 0.001% | 80 | 100 | 0 | 10 |
| Zinc Sulfadiazine in SILVADENE | 30 mM | 90 | 100 | 0 | 0 |
| Zinc Sulfadiazine in SILVADENE | 15 mM | 100 | 100 | 0 | 0 |
| Zinc Sulfadiazine and Cerium Sulfadiazine in SILVADENE | 15 mM each | 100 | 100 | 0 | 40 |
| Sulfamylon Acetate | | 60 | 100 | 71 | 100 |
| Silver Nitrate and Cerium Sulfadiazine | 1% + 30 mM | 50 | 100 | 0 | 0 |
| Silver Nitrate | 1% | 100 | 100 | — | — |
| Chlorhexidene | 1% | 80 | 100 | 0 | — |
| Furacin | 0.2% | 90 | 100 | 80 | 90 |
| Silver Sulfadiazine in Travase | 1% | 80 | 100 | — | — |
| Silver Phosophoformate | 1.6% | 80 | 100 | — | — |
| Gentamicin Sulfadiazine | 0.1% | 100 | 100 | 55 | 91 |
| CoSD, CeSD, ZnSd, AgSd | 30 mM | 80 | 80 | — | — |

[1] Trademark for silver sulfadiazine with a cream carrier manufactured and sold by Marion Laboratories, Inc., Kansas City, Missouri 64137

TABLE 5

Topical Therapy of Burned and Infected Mice with the Carboxylic Acid

| Groups | *No. of Mice | % Mortality (Days Post Burn) | | | | | | |
|---|---|---|---|---|---|---|---|---|
| | | 2 | 3 | 4 | 5 | 6 | 7 | 8 |
| Control | 45 | 67 | 87 | 100 | — | — | — | — |
| Rx 30 mM AgSD | 45 | 47 | 60 | 70 | 80 | 87 | 87 | 87 |
| Rx 3-6mM carboxylic acid | 25 | 8 | 8 | 12 | 12 | 24 | 24 | 32 |
| Rx 10 mM carboxylic acid | 22 | 0 | 0 | 0 | 0 | 0 | 0 | 0 |
| Rx 30 mM carboxylic acid | 10 | 0 | 0 | 0 | 0 | 0 | 0 | 0 |

*This is a summary of 3 groups of burned mice infected with different silver sulfadiazine resistant pseudomonas strains, viz: *Ps. Mangalore*, Ps. 181 and AgSD resistant *Ps. Boston*.

In contrast, in the groups of mice receiving topical therapy with the carboxylic acid, the mortality was 0% for both Ps. Mangalore and Ps. 181 infection when the concentration of the drug in the cream was 10 mM/kg. When lower amounts were used, there was 20-40 percent mortality.

In Vitro and In Vivo Efficacy of the Carboxylic Acid and its Silver Salt

In Vitro Assay:

Minimum inhibitory concentration of AgSD, carboxylic acid, and the silver salt thereof, against various organisms.

| Organism | AgSD | Drug (μmole/ml) | |
|---|---|---|---|
| | | carboxylic acid | silver salt of carboxylic acid |
| Ps. Boston | .05 | 0.004 | 0.003 |
| Ps. Mangalore | .05 | 0.008 | 0.003 |
| E. Coli | 0.0125 | (less than 0.006) | (less than 0.004) |
| Hemolytic Staph. | 0.5 | 0.003 | 0.003 |
| Klebsiella | 0.5 | 0.001 | (less than 0.0008) |

Mol. wt. of carboxylic acid = 309
Mol. wt. of silver salt of carboxylic acid = 415

5 ml of nutrient broth containing different concentrations of the drugs was inoculated with 0.2 ml of $10^{-4}$ dilution of the overnight culture. The cultures were incubated for 24 hours and the growth measured by turbidity.

In Vivo Efficacy:

Mice anesthetized with ether were given a 30% scald by dipping the lower third of their body into a water bath at 67° C. for 7 seconds. One hour past burn mice were given 1 ml of Normosol by I.P. injection and then infected by dipping the tail in an overnight culture of pseudomonas diluted to 0.30 O.D. at 600 nm.

The animals were divided at random into groups of 5 and topical therapy was initiated 4 hours post infection. Thereafter they were treated once daily. The primary criterion was survival. Animals that succumbed were autopsied and their cardiac blood was cultured to verify the presence of *pseudomonas sepsis*.

The results were as follows:

| Drug | Cage | No. | Days Post Burn | | | | |
|---|---|---|---|---|---|---|---|
| | | | 2 | 3 | 5 | 6 | 7 |
| | | | dead (%) | | | | |
| *Ps. Boston* infection: | | | | | | | |
| Control | 1 | 5 | 4 (80) | 1 (100) | — (100) | — (100) | |
| Topical AgSD | 2 | 5 | 3 (60) | 0 (60) | 1 (80) | 0 (80) | |
| 30 mM/kg carboxylic acid | 3 | 5 | 0 (0) | 0 (0) | 0 (0) | 0 (0) | |
| 30 mM/kg silver salt of carboxylic acid | 4 | 5 | 0 (0) | 0 (0) | 0 (0) | 0 (0) | |
| *Ps. Boston* and *Ps. Mangalore* Infection | | | | | | | |
| *Ps. Boston* | | | | | | | |
| Control | A | 5 | 5 (100) | — (100) | — (100) | — (100) | |
| Topical AgSD | B | 5 | 1 + 1 (40) | 1 (60) | 0 (60) | 0 (60) | |
| *Ps. Mangalore* | | | | | | | |
| Control | C | 4 | 4 (100) | — (100) | — (100) | 0 (100) | |
| Topical AgSD | D | 4 | 1 (25) | 0 (25) | 1 (50) | 1 (75) | |
| 5% Sulfamylon in Marion Base[2] | E | 4 | 2 + 2 (100) | — (100) | — (100) | — (100) | |
| 1% Sulfamylon in Silvadene | F | 4 | 1 (25) | 0 (25) | 1 (50) | 0 (50) | |
| 30 mM/kg carboxylic acid | G | 5 | 0 (0) | 0 (0) | 0 (0) | 0 (0) | |
| 30 mM/kg silver salt of carboxylic acid | H | 5 | 0 (0) | 0 (0) | 0 (0) | 0 (0) | |
| 6 mM/kg silver salt of carboxylic acid | I | 4 | 0 (0) | 0 (0) | 0 (0) | 0 (0) | 1 (25) |

[2]Cream used for Silvadene, see footnote 1, supra.

What is claimed is:

1. A metal salt of 1-ethyl-6-fluoro-1,4-dihydro-4-oxo-7-(1-piperazinyl)-3-quinoline carboxylic acid wherein the metal moiety is selected from the group consisting of silver, zinc, cerium, and cobalt.

2. A metal salt in accordance with claim 1 wherein the metal moiety is silver.

3. A metal salt in accordance with claim 1 wherein the metal moiety is zinc.

4. A metal salt in accordance with claim 1 wherein the metal moiety is cerous.

5. A method of treating surface bacterial infections in animal or man which comprises applying a composition containing an effective antibacterial amount of a metal salt of 1-ethyl-6-fluoro-1,4-dihydro-4-oxo-7-(1-piperazinyl)-3-quinoline carboxylic acid and a physiologically acceptable carrier to the affected surface, the metal moiety of said metal salt being selected from the group consisting of silver, zinc, cerium, and cobalt.

6. A method of treating burns in animal or man which comprises topically applying an effective antibacterial amount of the metal salt of claim 1 to the affected surface.

7. A composition useful for treating burns which comprises an effective amount of a metal salt in accordance with claim 1 and a physiologically acceptable carrier.

8. A method of treating burns in animal or man which comprises topically applying an effective antibacterial amount of the composition of claim 7 to the affected surface.

9. A composition in accordance with claim 7 wherein said effective amount is an amount from about 0.01 to about 1.0 percent by weight.

10. A composition in accordance with claim 7 wherein said physiologically acceptable carrier is a water-dispersible hydrophilic carrier.

11. A composition in accordance with claim 7 wherein said physiologically acceptable carrier is a semi-soft or cream-like, water-dispersible or water-soluble oil-in-water emulsion carrier.

12. A composition useful for treating burns which comprises an effective amount of the silver salt of claim 2 and a physiologically acceptable carrier.

13. A composition in accordance with claim 12 wherein said effective amount is an amount from about 0.01 to about 1.0 percent by weight.

14. A composition in accordance with claim 12 wherein said physiologically acceptable carrier is a water-dispersible hydrophilic carrier.

15. A composition in accordance with claim 12 wherein said physiologically acceptable carrier is a semi-soft or cream-like, water-dispersible or water-soluble oil-in-water emulsion carrier.

16. A composition useful for treating burns which comprises an effective amount of the zinc salt of claim 3 and a physiologically acceptable carrier.

17. A composition in accordance with claim 16 wherein said effective amount is an amount from about 0.01 to about 1.0 percent by weight.

18. A composition in accordance with claim 16 wherein said physiologically acceptable carrier is a water-dispersible hydrophilic carrier.

19. A composition in accordance with claim 16 wherein said physiologically acceptable carrier is a semi-soft or cream-like, water-dispersible or water-soluble oil-in-water emulsion carrier.

20. A method of treating burns in animal or man which comprises topically applying an effective antibacterial amount of the composition of claim 2 to the affected surface.

21. A method of treating burns in animal or man which comprises topically applying the composition of claim 16 to the affected surface.

22. A method of treating burns in animal or man which comprises topically applying the composition of claim 12 to the affected surface.

23. A method of treating burns in animal or man which comprises topically applying the composition of claim 7 to the affected surface.

* * * * *